US006310219B1

(12) United States Patent
Sawaki et al.

(10) Patent No.: US 6,310,219 B1
(45) Date of Patent: Oct. 30, 2001

(54) PROCESS FOR THE PRODUCTION OF MALEIC ANHYDRIDE

(75) Inventors: Itaru Sawaki; Hideo Suwa; Yasunori Ishimura, all of Okayama; Yoshiaki Iizuka; Mineo Izumi, both of Kanagawa, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/450,126

(22) Filed: Nov. 26, 1999

(30) Foreign Application Priority Data

Nov. 27, 1998 (JP) .................................................. 10-337356

(51) Int. Cl.⁷ ................................................ C07D 307/60
(52) U.S. Cl. ........................... 549/259; 549/257; 549/258; 549/260
(58) Field of Search ...................... 549/258, 259

(56) References Cited

U.S. PATENT DOCUMENTS

| 3,899,516 | 8/1975 | Dickason | 549/259 |
|---|---|---|---|
| 3,904,652 | 9/1975 | Frank | 549/259 |
| 4,222,945 | 9/1980 | Higgins et al. | 252/437 |
| 4,231,943 | 11/1980 | Paradis et al. | 549/259 |
| 4,259,246 | 3/1981 | Bakshi et al. | 549/259 |
| 4,317,777 | 3/1982 | Higgins et al. | 549/259 |
| 4,342,699 | 8/1982 | Palmer et al. | 549/259 |
| 4,352,755 | 10/1982 | Higgins et al. | 549/259 |
| 4,668,802 | 5/1987 | Contractor | 549/259 |
| 4,868,330 | 9/1989 | Ramachandran et al. | 558/320 |
| 4,987,239 | 1/1991 | Ramachandran et al. | 549/262 |
| 5,011,945 | 4/1991 | Taheri | 549/260 |
| 5,126,463 | 6/1992 | Ramachandran et al. | 549/259 |
| 5,179,215 | 1/1993 | Ramachandran et al. | 549/262 |
| 5,262,547 | 11/1993 | Ramachandran et al. | 549/259 |
| 5,278,319 | 1/1994 | Ramachandran et al. | 549/262 |
| 5,532,384 | 7/1996 | Shirley et al. | 549/257 |
| 5,646,304 | 7/1997 | Acharya et al. | 549/259 |
| 5,688,970 | 11/1997 | Ruggieri et al. | 549/262 |
| 5,726,327 | 3/1998 | Acharya et al. | 549/259 |

FOREIGN PATENT DOCUMENTS

| 0 099 431 | 2/1984 | (EP) . |
|---|---|---|
| 0 486 286 A2 | 5/1992 | (EP) . |
| 0 745 578 A1 | 12/1996 | (EP) . |
| 1 450 986 | 9/1976 | (GB) . |
| 49-102615 | 9/1974 | (JP) . |
| 50-40514 | 4/1975 | (JP) . |
| WO 99/67021 | 12/1999 | (WO) . |
| WO 99/67194 | 12/1999 | (WO) . |

OTHER PUBLICATIONS

John J. McKetta, et al., "Fire Extinguishing Chemicals to Fluid Flow, Slurry Systems and Pipelines", Encyclopedia of Chemical Processing and Design, pp. 119–122.

Gabriele Centi, et al., "Mechanistic Aspects of Maleic Anhydride Synthesis from $C_4$ Hydrocarbons Over Phosphorus Vanadium Oxide", Chem. Rev. 1988, 88, pp. 55–80.

U.S. application No. 09/119,723, filed Jul. 21, 1998, pending.

U.S. application No. 09/450,126, Nov. 26, 1999, pending.

*Primary Examiner*—Bernard Dentz
(74) *Attorney, Agent, or Firm*—Oblon, Spivak, McClelland, Maier & Neustadt, P.C.

(57) ABSTRACT

Disclosed is a process for the production of maleic anhydride, which comprises: reacting a hydrocarbon with an oxygen-containing gas in the presence of a catalyst; recovering maleic anhydride from the reaction gas; recovering unreacted hydrocarbon from the remaining gas; and returning the hydrocarbon thus recovered to the reactor for re-use, wherein said reaction is effected under the conditions such that the hydrocarbon concentration X (vol %) and oxygen concentration Y (vol %) in all the gases to be fed into the reactor, the hydrocarbon conversion Z (%) in the reactor and the oxygen concentration W (vol %) in all the effluent gases from the reactor satisfy the following relationships:

$Y \geq 20$, $X+Y \leq 70$, $1 \leq Y/X \leq 5$, and $20(Y-10)/X \leq Z \leq 25Y/X$ or $2 \leq W \leq 10$.

9 Claims, No Drawings

PROCESS FOR THE PRODUCTION OF MALEIC ANHYDRIDE

TECHNICAL FIELD OF THE INVENTION

The present invention relates to a process for the production of maleic anhydride by subjecting a hydrocarbon to catalytic oxidation in a gas phase. More particularly, the present invention relates to a process for the production of maleic anhydride which comprises recovering a hydrocarbon left unreacted in a reactor, and then returning the hydrocarbon thus recovered to the reactor where it is then subjected to catalytic oxidation under specific reaction conditions.

BACKGROUND ART

It is well known to produce maleic anhydride by subjecting a hydrocarbon to catalytic oxidation in a gas phase. Heretofore, the production of maleic anhydride has been accomplished by the reaction of benzene and air as raw materials in the presence of a vanadium pentoxide-based catalyst. In recent years, processes involving the use of a straight-chain hydrocarbon having four carbon atoms such as butane, butene and butadiene have been developed. Among these processes, one involving the reaction of n-butane, which is a saturated hydrocarbon, as a raw material in the presence of a catalyst comprising a vanadium-phosphorus mixed oxide as an active component has been mainly employed. As the active component to be incorporated in such a catalyst, divanadyl pyrophosphate ($(VO)_2P_2O_7$) has been known to exhibit excellent performance. Many references concerning this compound have been published (e.g., Chem. Rev. 88, p. 55–80 (1988)).

The foregoing reaction is effected in a fluidized bed process or a fixed bed process. In some detail, a hydrocarbon and an oxygen-containing gas, normally air, are fed as raw material into a reactor in such a manner that the concentration of the hydrocarbon reaches from about 1.5 to 10%. The reaction mixture is then allowed to undergo reaction at a temperature of from 300° C. to 600° C. The reaction gas coming out of the reactor contains maleic anhydride as well as carbon monoxide, carbon dioxide, water and other reaction products. The separation and recovery of maleic anhydride from the reaction gas is accomplished by a process which comprises cooling the reaction gas to condense maleic anhydride, a process which comprises allowing the reaction gas to come in contact with water so that maleic anhydride is collected as maleic acid in water, a process which comprises allowing the reaction gas to come in contact with an organic solvent such as phthalic acid ester or alkyl ester of hydrogenated phthalic acid so that maleic anhydride is collected in the organic solvent.

In the commercially practiced process for the production of maleic anhydride, the hydrocarbon conversion in the reactor [number of mole of hydrocarbon consumed in the reaction per pass/number of mols of hydrocarbon supplied into the reactor×100 (mol %)] is kept as high as possible. This is required to minimize the amount of hydrocarbon as a raw material required to produce maleic anhydride. In general, the hydrocarbon left unreacted in the reactor is incinerated in a waste gas burning apparatus.

On the other hand, it has been known to reduce the hydrocarbon conversion, making it possible to reduce the proportion of carbon monoxide or carbon dioxide to be produced as a by-product and hence enhance the maleic anhydride selectivity [number of mols of maleic anhydride produced by the reaction/number of mols of hydrocarbon consumed in the reaction×100 (mol %)]. Accordingly, if the hydrocarbon conversion can be kept low and the hydrocarbon left unreacted can be recovered and again supplied for reaction as a raw material, the unreacted hydrocarbon which would otherwise be incinerated and the hydrocarbon which would otherwise be converted to carbon monoxide or carbon dioxide can be partly converted to maleic anhydride, making it possible to drastically reduce the amount of hydrocarbon to be consumed as a raw material in the production of a unit amount of maleic anhydride. Therefore, this process is an extremely fascinating on an economical basis.

The foregoing process is also advantageous in that the recovery of the unreacted hydrocarbon which would be otherwise incinerated makes it possible to drastically reduce the amount of gas to be wasted during the production of maleic anhydride, particularly the emission of carbon dioxide, which is one of the greenhouse effect gases the emission of which has recently faced a growing demand for reduction, and hence drastically reduce the influence on the environment.

In practice, JP-A-49-81314 (The term "JP-A" as used herein means an "unexamined published Japanese patent application"), JP-A-54-151910 and JP-A-59-29679 propose a process which comprises reducing the hydrocarbon conversion in the reactor to keep the maleic anhydride selectivity high while the unreacted hydrocarbon is being partly recovered and returned to the reactor.

However, none of these proposals have ever been commercially practiced. This is because the hydrocarbon concentration needs to be higher than ever to prevent the drop of the productivity of maleic anhydride while keeping the conversion in the reactor low. If the hydrocarbon concentration is higher than ever, high temperature portions called "hot spot" occur in the reactor, causing degradation of catalyst. This is also because when the unreacted hydrocarbon is recovered, carbon monoxide or carbon dioxide produced as by-product, too, is recovered, making it necessary to use large amount of pure oxygen or oxygen enriched air, which is an expensive oxygen source, due to restrictions on material balance.

Further, economically favorable reaction conditions differ greatly from that of the conventional once through reaction. Thus, the criteria of explosion safety of the feed gas to, or the effluent gas from the reactor, product recovering apparatus or hydrocarbon recovering apparatus greatly differ. The foregoing proposals contain reference to the safety of the reactor feed gas but have no reference to the safety of the entire recycle process.

On the other hand, JP-A-1-165564 proposes a process which comprises returning unreacted hydrocarbon recovered by an apparatus for selectively separating hydrocarbon to a reactor wherein the content of flame suppressor is regulated to prevent a mixture of hydrocarbon and oxygen from producing a flammable mixture. However, this proposal regulates the safety of the stream from the reaction apparatus to the hydrocarbon recovering apparatus and back to the reaction apparatus but doesn't suffice for the safety of the entire process for the production of maleic anhydride. In other words, it is substantially difficult to completely recover hydrocarbon by the hydrocarbon recovering apparatus. Thus, the exhaust gas after recovering hydrocarbon is a mixed gas containing flammable gases such as hydrocarbon and carbon monoxide and oxygen. Accordingly, the explosion safety of the mixed gas must be considered.

In accordance with economically favorable conditions under which a high productivity can be realized, that is, the concentration of maleic anhydride in the reaction gas can reach not less than 2 vol %, the concentration of carbon monoxide in the reaction gas, too, is higher than under the conventional conditions. Accordingly, the exhaust gas after recovering hydrocarbon has a higher carbon monoxide concentration than the conventional composition the safety of which has heretofore been known. Thus, it is likely that the explosive region of the exhaust gas is expected to be wider. Nevertheless, no specific methods for controlling the explosion safety have been known.

In other words, some methods have been proposed which comprise recovering and recycling unreacted hydrocarbon to the rector while keeping the hydrocarbon conversion in the reactor low to enhance the maleic anhydride selectively for the purpose of efficiently producing maleic anhydride. However, all the foregoing proposals are disadvantageous in that the use of pure oxygen or oxygen enriched air, which is expensive, adds to the production cost and the enhancement of productivity is accompanied by the generation of enormous heat that deteriorates the performance of the catalyst. These proposals are also disadvantageous in respect to safety control. Thus, these proposals are not necessarily excellent methods. In actuality, these proposals have never been commercially practiced.

SUMMARY OF THE INVENTION

The present invention has been worked out for the purpose of providing reaction conditions required for the production of economically excellent maleic anhydride and conditions required for securing safety in a process which comprises allowing a hydrocarbon and an oxygen-containing gas to undergo reaction in the presence of a catalyst to produce maleic anhydride, recovering maleic anhydride from the reaction gas, recovering the hydrocarbon left unreacted from the remaining gas, and then returning the unreacted hydrocarbon to the reactor for re-use.

The inventors made extensive studies of the foregoing problems. As a result, it was found that when the reaction is effected with the concentration of hydrocarbon and oxygen in the gas to be fed into the reactor and the conversion of hydrocarbon in the reaction combined under predetermined conditions, the productivity of maleic anhydride can be enhanced while keeping the amount of hydrocarbon to be consumed as a raw material low, making it possible to produce maleic anhydride on an economical basis. Further, paying attention to the concentration of oxygen, hydrocarbon and carbon monoxide in the exhaust gas after recovering hydrocarbon at the hydrocarbon recovery step, a gas explosion experiment was repeated. As a result, it was found that when the relationship between these gas concentrations is kept under predetermined conditions, safety can be secured. The present invention has been worked out on the basis of this knowledge.

The present invention provides a process for the production of maleic anhydride which comprises a reaction step for reacting a hydrocarbon with an oxygen-containing gas in the presence of a catalyst, a maleic anhydride recovering step for recovering maleic anhydride from the reaction gas, a hydrocarbon recovering step for recovering unreacted hydrocarbon from the remaining gas and a recycling step for returning the hydrocarbon thus recovered to the reactor for re-use, characterized in that said reaction is effected under the conditions such that the hydrocarbon concentration X (vol %) and oxygen concentration Y (vol %) in all the gases to be fed into the reactor, the hydrocarbon conversion Z (%) in the reactor and the oxygen concentration W (vol %) in all the effluent gases from the reactor satisfy the following relationships:

$Y \geq 20$, $X+Y \leq 70$, $1 \leq Y/X \leq 5$, and $20(Y-10)/X \leq Z \leq 25Y/X$ or $2 \leq W \leq 10$.

In another embodiment of the present invention, a process for the production of maleic anhydride is provided which comprises a reaction step for reacting a hydrocarbon with an oxygen-containing gas in the presence of a catalyst, a maleic anhydride recovering step for recovering maleic anhydride from the reaction gas, a hydrocarbon recovering step for recovering unreacted hydrocarbon from the remaining gas and a recycling step for returning the hydrocarbon thus recovered to the reactor for re-use, characterized in that the concentration of maleic anhydride in the reaction gas is not less than 2 vol % and the oxygen concentration A (vol %), hydrocarbon concentration B (vol %) and carbon monoxide concentration C (vol %) in the exhaust gas after recovering unreacted hydrocarbon at the hydrocarbon recovering step, satisfy the following requirements:

$D=C/(B+C)$, $E=100A/(100-B-C)$, and $0<\alpha<10$, in which $\alpha=-10.51+51.22D-35.35D^2-E$.

In a preferred embodiment of the present invention, a process for the production of maleic anhydride is provided which comprises a reaction step for reacting a hydrocarbon with an oxygen-containing gas in the presence of a catalyst, a maleic anhydride recovering step for recovering maleic anhydride from the reaction gas, a hydrocarbon recovering step for recovering unreacted hydrocarbon from the remaining gas and a recycling step for returning the hydrocarbon thus recovered to the reactor for re-use, characterized in that (a) said reaction is effected under the conditions such that the hydrocarbon concentration X (vol %) and oxygen concentration Y (vol %) in all the gases to be fed into the reactor, the hydrocarbon conversion Z (%) in the reactor and the oxygen concentration W (vol %) in all the effluent gases from the reactor satisfy the following relationships:

$Y \geq 20$, $X+Y \leq 70$, $1 \leq Y/X \leq 5$, and $20(Y-10)/X \leq Z \leq 25Y/X$ or $2 \leq W \leq 10$, and (b) the oxygen concentration A (vol %), hydrocarbon concentration B (vol %) and carbon monoxide concentration C (vol %) in the exhaust gas after recovering unreacted hydrocarbon at the hydrocarbon recovering step satisfy the following requirements:

$D=C/(B+C)$, $E=100A/(100-B-C)$, and $0<\alpha<10$, in which $\alpha=-10.51+51.22D-35.35D^2-E$.

DETAILED DESCRIPTION OF THE INVENTION

Preferred Embodiment

The present invention will be further described hereinafter.

As mentioned above, the present invention provides a process for the production of maleic anhydride which comprises a reaction step for reacting a hydrocarbon with an oxygen-containing gas in the presence of a catalyst, a maleic anhydride recovering step for recovering maleic anhydride from the reaction gas, a hydrocarbon recovering step for recovering unreacted hydrocarbon from the remaining gas and a recycling step for returning the hydrocarbon thus recovered to the reactor for re-use, characterized in that said reaction is effected with the concentration of hydrocarbon and oxygen in the gas to be fed into the reactor, the hydrocarbon conversion in the reaction and the oxygen concentration in all the effluent gases from the reactor combined under predetermined conditions and the relationship among the concentration of oxygen, hydrocarbon and carbon monoxide in the exhaust gas after recovering unreacted hydrocarbon at the hydrocarbon recovering step satisfies predetermined conditions.

In the production process of the present invention, maleic anhydride is produced at a reaction step for reacting a hydrocarbon with an oxygen-containing gas in the presence of a catalyst in a reactor.

As the hydrocarbon to be used as a raw material at the foregoing reaction step there is preferably used a hydrocarbon having four carbon atoms such as butane, butene and butadiene. Particularly preferred among these hydrocarbons is n-butane, which is a saturated hydrocarbon having four carbon atoms. As the oxygen-containing gas there is normally used air. Further, air diluted with an inert gas, air enriched with oxygen or the like may be used.

As the catalyst there is preferably used one comprising as an active component a mixed oxide containing vanadium and phosphorus as main constituents (hereinafter occasionally referred to as "vanadium-phosphorus mixed oxide-based catalyst"). These catalysts themselves are well known and commonly used. For example, such a catalyst can be prepared by the method described in U.S. Pat. Nos. 4,520,127 and 4,472,527, and JP-A-7-68179.

As the reactor there may be used a commonly used fixed bed reactor or fluidized bed reactor. However, the fluidized bed reactor is preferable due to its insusceptibility to problem of explosion of the reactor feed gas and generation of hot spots.

The fluidized bed reactor to be used herein may be in the form of ordinary structure comprising a gas dispersing plate provided at the bottom of the reactor defining the lower end of the catalyst fluidized bed, a raw material gas feed port provided in the lower zone of the catalyst fluidized bed and a particle recovering apparatus such as cyclon collector and/or filter system provided at the top or outlet of the reactor. Preferably, the reactor is further provided with an indirect heat exchanger for cooling the reaction product gas such as cooling coil at the position where the catalyst fluidized bed is to be formed.

In the process of the present invention, the vanadium-phosphorus mixed oxide-based catalyst on the gas dispersing plate becomes fluidized by the gas which has been fed from below the gas dispersing plate in the reactor to form a dense fluidized bed above the gas dispersing plate. The heat generated by the reaction is removed by the heat exchanger provided in the fluidized bed to control the reaction temperature. The reaction temperature is normally from about 330° C. to 500° C., preferably from about 360° C. to 460° C. In this arrangement of catalyst fluidized bed, the hydrocarbon as raw material undergoes catalytic oxidation in a gas phase to produce maleic anhydride in the reaction product gas.

The reaction product gas contains maleic anhydride as desired compound as well as unreacted oxygen and hydrocarbon and by-products, including carbon dioxide, water and carbon monoxide, in various concentrations. The reaction product gas comes out of the catalyst fluidized bed together with the catalyst, and then is introduced into the particle recovering apparatus such as cyclon provided at the top or outlet of the reactor where it is then separated from the entrained catalyst and withdrawn. The catalyst separated from the reaction product gas in the particle recovering apparatus is returned to the fluidized bed, if desired. Maleic anhydride is separated and recovered from the reaction product gas thus withdrawn (maleic anhydride recovering step).

The concentration of maleic anhydride in the reaction product gas is not specifically limited. However, it is preferably not less than 2.0 vol %, more preferably not less than 2.5 vol %, even more preferably not less than 3.0 vol %. By keeping the concentration of maleic anhydride in the reaction product gas high, the amount of gas to be circulated in the recycle process can be reduced.

The separation and recovery of maleic anhydride can be accomplished by any commonly used method known as such, e.g., method which comprises cooling the reaction gas to condense maleic anhydride, method which comprises allowing the reaction gas to come in contact with water to collect maleic anhydride in water as maleic acid, method which comprises allowing the reaction gas to come in contact with an organic solvent such as phthalic acid dialkyl ester or alkyl ester of hydrogenated phthalic acid (e.g., tetrahydrophthalic acid, hexahydrophthalic acid) to collect maleic anhydride in the organic solvent.

The raw material hydrocarbon left unreacted is then recovered from the remaining gas after separating and recovering maleic anhydride (hydrocarbon recovering step). The hydrocarbon thus recovered at the hydrocarbon recovering step is then returned to the reactor for re-use (recycling step). A fresh oxygen-containing gas and a hydrocarbon are fed into the reactor in such an amount that the total amount of gases to be fed into the reactor and the concentrations of oxygen and hydrocarbon in all the feed gases are kept at predetermined values.

If gases other than the raw material hydrocarbon are recovered at the hydrocarbon recovering step, the amount of air which can be used as an oxygen source to be fed into the reactor must be restricted. In other words, if nitrogen, carbon monoxide or carbon dioxide is recovered together with hydrocarbon at the hydrocarbon recovering step, the amount of inert gases (i.e., gases other than hydrocarbon and oxygen) to be returned to the reactor is increased so much. The total amount of inert gases which can be fed into the reactor is determined depending on the concentration of hydrocarbon and oxygen. The value obtained by subtracting the amount of inert gases to be recycled to the reactor from the total amount of inert gases which can be fed into the reactor is the amount of inert gas which can be freshly fed into the reactor. Thus, when air is used as an oxygen source, the amount of nitrogen accompanied with air to be fed is restricted. As a result, the amount of air which can be fed into the reactor is remarkably restricted, making it necessary to use pure oxygen or oxygen enriched air as an oxygen source.

The foregoing problem can be solved by the use of a method enabling the selective recovery of hydrocarbon as a method for recovering the raw material hydrocarbon. The term "selective" as used herein is meant to indicate that more than about half the amount of gases other than hydrocarbon is not recovered while recovering the majority (more than about 90%) of hydrocarbon. This selective recovery of hydrocarbon makes it possible to maximize the utilization of air, which is an inexpensive oxygen source to be fed into the reactor. However, even this method can hardly eliminate the necessity of using pure oxygen or oxygen enriched air. This is because the process of the present invention unavoidably requires the use of some amount of pure oxygen or oxygen enriched air to meet the requirements for high concentration of hydrocarbon and oxygen in all the gases to be fed into the reactor for the purpose of remarkably enhancing the productivity of maleic anhydride as described later.

However, in accordance with the process of the present invention, the economical advantage developed by a drastic drop of the amount of hydrocarbon consumed as a raw material overwhelms the disadvantage developed by the use of a small amount of pure oxygen or oxygen enriched air. Further, the cost reduction developed by the enhancement of the productivity of maleic anhydride that allows the drop of the recycled amount of gas and the load on the waste gas incinerator overwhelms the cost rise developed by the introduction of the apparatus for selectively separating and recovering hydrocarbon. Accordingly, the entire production cost of maleic anhydride can be reduced.

As the apparatus for selectively separating and recovering hydrocarbon there may be used any commonly used membrane type separating apparatus or adsorption-separation type apparatus known as such, e.g., PSA (pressure swing adsorption apparatus), VSA (vacuum swing adsorption apparatus), TSA (temperature swing adsorption apparatus). If such an adsorption-separation type apparatus is used, a method may be employed involving the use of an adsorbent capable of selectively separating and recovering hydrocarbon such as zeolite or silicalite as disclosed in JP-A-8-325256 and U.S. Pat. No. 4,987,239.

The remaining gas after separating and recovering maleic anhydride can partly be directly returned to the reactor without being passed through the hydrocarbon separating/recovering apparatus. This arrangement causes gases other than hydrocarbon such as carbon dioxide, carbon monoxide and nitrogen to be recycled to the reactor but makes it possible to reduce the size of the hydrocarbon separating/recovering apparatus.

The point which should be noted to produce maleic anhydride more economically than ever in the foregoing process for the production of maleic anhydride which comprises returning the unreacted hydrocarbon gas to the reactor for re-use is how much the consumed amount of raw material hydrocarbon and the amount of gas to be recycled in the system can be reduced. In order to meet the foregoing requirements, it is effective to keep the conversion in the reactor low, thus enhancing the maleic anhydride selectivity, and at the same time to increase the concentration of maleic anhydride in the reaction product gas.

In the case where the concentration of raw material hydrocarbon in all the gases to be fed into the reaction system is the same, if the conversion of raw material hydrocarbon is reduced, the concentration of maleic anhydride in the reactor effluent gas (hereinafter referred to as "productivity") is reduced even if the maleic anhydride selectivity is enhanced. This means that it is necessary to raise the concentration of hydrocarbon in all the gases to be fed into the reaction system higher than ever in order to obtain a productivity which is equal to or higher than the conventional value in the process for the reduction of the hydrocarbon conversion in the reactor.

In the case where maleic anhydride is prepared from n-butane, which is a saturated hydrocarbon having four carbon atoms, carbon monoxide, carbon dioxide, etc. are normally produced as by-products. As a result, oxygen is consumed in a total amount of from 3.8 to 4.9 mols per mol of n-butane in the entire reaction involving the production of maleic anhydride, carbon monoxide, carbon dioxide, water, etc. from n-butane.

However when the butane concentration is high to enhance the productivity, if oxygen is not present in an amount high enough for reaction, oxygen is earlier consumed completely, making it impossible to enhance the concentration of maleic anhydride in the reaction gas. In other words, it is necessary to supply oxygen into the reactor in an amount of at least from 3.8 to 4.9 times the amount of butane to be consumed in the reaction while increasing the butane concentration in order to enhance the productivity.

On the other hand, the inventors found that the maleic anhydride selectivity is greatly effected not only by the hydrocarbon conversion but also by the concentration of hydrocarbon and oxygen in the gas to be supplied into the reaction. The results show that the reduction of the hydrocarbon conversion causes the enhancement of the maleic anhydride selectivity while the increase of the hydrocarbon concentration in the reactor feed gas as well as the decrease of the oxygen concentration in the reactor feed gas cause the drop of maleic anhydride selectivity. This demonstrates that the ratio of oxygen concentration to hydrocarbon concentration in the reactor feed gas is an important factor determining the maleic anhydride selectivity.

Accordingly, it is extremely important to select optimum conditions from various combinations of the concentration of hydrocarbon and oxygen in the reactor feed gas and the hydrocarbon conversion in the reaction in order to enhance the productivity while keeping the consumed amount of raw material hydrocarbon low.

In other words, the inventors succeeded in finding the optimum conditions by measuring the maleic anhydride selectivity over various hydrocarbon concentrations, oxygen concentrations and hydrocarbon conversions and evaluating the economical efficiency of the entire process under the various conditions.

Thus, in the present invention, when the hydrocarbon concentration in all the gases to be fed into the reactor is sufficiently high, the oxygen concentration is an important factor determining the productivity. Accordingly, in order to enhance the productivity higher than ever, it is necessary that the oxygen concentration (Y: vol %) be not less than 20 vol %, preferably not less than 25 vol %. The higher the oxygen concentration is, the higher can be enhanced the productivity. In order to increase the oxygen concentration, it is necessary to use increased amount of pure oxygen or oxygen enriched air, which is expensive. Thus, it is required that the oxygen concentration be substantially kept not greater than 50 vol %, preferably not greater than 40 vol %.

On the other hand, the hydrocarbon concentration in all the gases to be fed into the reactor (X: vol %) needs to be arranged such that the ratio of the oxygen concentration to the hydrocarbon concentration (Y/X) is kept at a range of from 1 to 5. If Y/X falls below 1, that is, the hydrocarbon concentration is greater than the oxygen concentration, the hydrocarbon conversion is decreased but the maleic anhydride selectivity drops. On the contrary, if Y/X exceeds 5, it is necessary to increase the hydrocarbon conversion in order to reduce the oxygen concentration at the outlet of the reactor so as to prevent the effluent gas from being kept in an explosive state. This, too, reduces the maleic anhydride selectivity. As a result, it is necessary that Y/X range from not less than 1 to not more than 5, preferably from not less than 1.2 to not more than 4.5, more preferably from not less than 1.5 to not more than 4 to keep the maleic anhydride selectivity high.

The higher the sum of the content of hydrocarbon and oxygen in all the gases to be fed into the reactor (X+Y) is, the higher is the productivity. However, it is not practical to increase the sum (X+Y) high than 70 vol %. This is because the increase in the sum of the content of hydrocarbon and oxygen means the reduction of the proportion of other gases such as nitrogen or carbon dioxide that limits the consumable amount of air, which is the most inexpensive oxygen source, resulting in the increase in the required amount of pure oxygen or oxygen enriched air, which is relatively expensive, and hence increasing the economical disadvantage. Therefore, the nitrogen concentration in all the gases to be fed into the reactor is at least 30 vol %, preferably at least 35 vol %.

Further, when hydrocarbon is recovered from at least a part of the remaining gas after recovering maleic anhydride from reactor effluent gas, and then returned to the reactor, it is not practical to recover only hydrocarbon even using an apparatus capable of selectively separating hydrocarbon. As a result, some amount of carbon dioxide or nitrogen must be returned to the reactor together with the hydrocarbon. The amount of carbon dioxide or nitrogen to be returned to the reactor together with the hydrocarbon restricts the sum of the amount of hydrocarbon and oxygen in the reactor feed gas.

For these reasons, the economically and practically possible range of the composition of the reactor feed gas was extensively studied. As a result, it was found that the sum (X+Y) needs to be not more than 70 vol %, preferably not more than 60 vol %, even more preferably not more than 50 vol %.

When the gas having the composition satisfying the foregoing requirements is fed into the reactor, the resulting hydrocarbon conversion must be from not less than 20(Y−10)/X to not more than 25Y/X. If the hydrocarbon conversion (Z: %) exceeds the above defined range, the maleic anhydride selectivity id dropped more than required. On the contrary, if the hydrocarbon conversion falls below the above defined range, the oxygen concentration in all the reactor effluent gases is too high, possibly causing the explosion of the effluent gas. By controlling the hydrocarbon conversion to keep the oxygen concentration in all the reactor effluent gases (W: vol %) to a range of from not less than 2 vol % to not more than 10 vol %, the same effect can be exerted.

In this recycle process, it is important to minimize the loss of hydrocarbon for the purpose of efficiently produce maleic anhydride. The percent recovery of hydrocarbon [number of mols of hydrocarbon recovered by the recovering apparatus/number of mols of hydrocarbon supplied into the recovering apparatus×100 (%)] is preferably not less than 90%, more preferably not less than 95%, even more preferably not less than 98%.

In the recycle process satisfying the foregoing requirements, the exhaust gas left after the hydrocarbon recovering step involving the recovery of unreacted hydrocarbon from the remaining gas after separating and recovering maleic anhydride from reactor effluent is a mixture gas containing carbon monoxide, hydrocarbon, oxygen, carbon dioxide and nitrogen. If hydrocarbon is selectively separated and recovered under preferred condition, the major flammable component in the exhaust gas is carbon monoxide with a slight amount of hydrocarbon.

In general, the safety of the mixture gas containing oxygen and a plurality of flammable gas components against explosion is determined by the concentration of oxygen, the concentration of the various flammable gas components, and the temperature and pressure of the mixture gas. However, no methods for accurately predicting the safety of a mixture of e.g., butane and carbon monoxide against explosion have been known. On the other hand, the composition of the gas to be fed into the hydrocarbon recovering step varies with the reaction conditions or results of reaction. Further, the composition of the exhaust gas after recovering hydrocarbon at the hydrocarbon recovering step varies with the hydrocarbon recovering conditions or results of recovery. In particular, if an adsorption-separation type hydrocarbon recovering apparatus is used, the composition of the effluent from the hydrocarbon recovering apparatus shows a cyclic variation. Thus, in order to invariably secure the explosion safety of the mixture gas, it is essential to invariably confirm by some means that the gas composition is in a safe state.

As methods for securing the explosion safety of a mixture of oxygen-containing gas and flammable gas there have normally been known three methods, i.e., method which comprises keeping the concentration of flammable gas at lower than the lower explosive limit, method which comprises keeping the concentration of flammable gas at higher than the upper explosive limit, method which comprises keeping the oxygen concentration at lower than the minimum oxygen concentration.

The foregoing method which comprises keeping the concentration of flammable gas component at lower than the lower explosive limit has heretofore been actually used in the process for the production of maleic anhydride. In other words, the lower explosive limit of mixed gas can be predicted by Le Chateliers law, which has heretofore been widely known to those skilled in the art (see "Encyclopedia of Chemical Processing and Design Volume 22", published by Marcel Dekker, Inc., page 120 (1985)). Thus, by comparing the monitored concentration of hydrocarbon and carbon monoxide with the lower explosive limit in the monitored composition calculated using Le Chateliers law, a predetermined safety margin can be invariably secured. This method not only has heretofore been employed to secure the safety of the remaining gas after recovering maleic anhydride from the reactor effluent but also can be applied to secure the safety of the exhaust gas after recovering hydrocarbon at the hydrocarbon recovering step in the recycle process depending on some conditions.

However, the study made by the inventors shows that the concentrations of flammable gases (sum of the concentration of hydrocarbon and carbon monoxide) in the exhaust gas after recovering hydrocarbon at the hydrocarbon recovering step can often exceed the lower explosive limit. This phenomenon becomes remarkable particularly under the conditions such that the concentration of maleic anhydride in the reaction gas increases. Under the conditions that the productivity is not less than 2 vol % as calculated in terms of maleic anhydride concentration, the method which comprises keeping the concentrations of flammable gases at lower than the lower explosive limit is substantially made difficult. This is because such condition produces carbon monoxide in a high concentration at the reaction step, thus the concentration of carbon monoxide in the exhaust gas from the hydrocarbon recovery step increases and when a small amount of unrecovered hydrocarbon is introduced into this stream, the concentration of flammable gas becomes equal to or greater than the lower explosive limit. In addition, if there occurs a composition change with time, particularly a cyclic or unexpected change in the concentration of hydrocarbon in the adsorption-separation type recovering apparatus, it is necessary to reduce the concentration of maleic anhydride at the reaction step and hence reduce the concentration of carbon monoxide co-produced or recover hydrocarbon in a higher percent recovery at the hydrocarbon recovering step in order to invariably secure sufficient safety margin. It is necessary at the same time to invariably monitor the gas composition accurately without delay in measurement.

Further, the exhaust gas after recovering hydrocarbon at the hydrocarbon recovering step is mainly composed of carbon monoxide as a flammable gas and thus has an extremely high upper explosive limit. Accordingly, it is substantially difficult to keep the concentration of flammable gas higher than the upper explosive limit.

On the other hand, it was made obvious that the method which comprises keeping the oxygen concentration in the exhaust gas after recovering hydrocarbon at the hydrocarbon recovering step lower than the minimum oxygen concentration can be sufficiently used as a safety control method even under the conditions such that the productivity of maleic anhydride is high.

The oxygen concentration of the exhaust gas can be indirectly controlled by controlling the conditions in the reaction step to control the reactor effluent oxygen concentration even under such a high maleic anhydride productivity conditions. Thus the oxygen concentration of the exhaust has can be easily kept lower than the minimum oxygen concentration at all the time.

The minimum oxygen concentration, too, is somewhat affected by the change in the flammable gas composition. However, the effect of the change in the flammable gas concentration on the minimum oxygen concentration is smaller than that on the lower explosive limit. Further, the object to be directly monitored is not the flammable gas concentration, the fluctuation of which is large, but the oxygen concentration, which is little liable to fluctuate even using the adsorption-separation type apparatus. Accordingly, the explosion safety of this stream can be easily managed by controlling the oxygen concentration always below the minimum oxygen concentration.

Then, the inventors experimentally determined the minimum oxygen concentration in the mixture of carbon monoxide and hydrocarbon, which has never been known, and found that explosion safety control can be made on the basis of this value. Thus, another embodiment of implication of the present invention has been attained.

In the present invention, in order to secure the safety of the exhaust gas after recovering hydrocarbon at the hydrocarbon recovering step, it is required that the concentration of oxygen, hydrocarbon and carbon monoxide in the exhaust gas (A (vol %), B (vol %) and C (vol %), respectively) satisfy the following requirements.

The safety coefficient $\alpha$ shall indicate a value calculated by the following equation (1):

$$\alpha = -10.51 + 51.22\,D - 35.35\,D^2 - E \quad (1)$$

where D indicates a value calculated by the following equation (2):

$$D = C/(B+C) \quad (2)$$

and E indicates a value calculated by the following equation (3):

$$E = 100\,A/(100 - B - C) \quad (3)$$

The safety coefficient also shall satisfy the following relationship:

$$0 < \alpha < 10$$

The safety coefficient $\alpha$ is a coefficient related to the minimum oxygen concentration in the oxygen-containing flammable gas mixture. The greater the safety coefficient $\alpha$ is, the more the current composition from the minimum oxygen concentration deviates, this means the condition is safer. Thus, when the safety coefficient $\alpha$ indicates a positive value, it can be said that the gas is safe. However, it is preferred that some margin be taken to the safety coefficient $\alpha$ taking into account the error in the analysis of various components or the lag in measurement. On the other hand, however, the productivity, catalyst life or operation cost needs to be sacrificed for increasing the safety coefficient $\alpha$. Thus, it is not practical to take an excessive margin. Accordingly, the safety coefficient $\alpha$ is preferably kept at a range of from more than 0 to less than 10, more preferably from more than 1 to less than 5.

The foregoing equation (1) is an empirical equation obtained by explosion experiments under various conditions. The temperature and pressure on which this equation is based range from normal temperature to 100° C. and atmospheric pressure to 0.1 MPa (gauge), respectively. The equation (1) is substantially effective, when the value of D in the foregoing equation (2) is from not less than 0.7 to not more than 1.0 as a result of the explosion experiments.

The oxygen concentration in the exhaust gas after recovering hydrocarbon at the hydrocarbon recovering step is preferably measured continuously by any commonly used oxygen analysis means known as such, e.g., on-line oxygen analyzer. The concentration of hydrocarbon and carbon monoxide in the exhaust gas are preferably measured continuously by any commonly used on-line monitor means known as such, e.g., infrared analyzer. The gas composition can be also measured by a discontinuous measuring means such as gas chromatograph. However, such a discontinuous measuring means is not desirable from the standpoint of safety control if the gas composition varies with time.

In particular, if an adsorption-separation type apparatus is used as the hydrocarbon recovering apparatus, the composition of the exhaust gas after recovering hydrocarbon shows a cyclic variation. Thus, it is preferred to confirm that the safety coefficient $\alpha$ falls within a predetermined range by invariably calculating the safety coefficient $\alpha$ on a real time basis using an analyzer capable of continuously measuring the concentrations of each component.

If the exhaust gas doesn't show a large composition change, the safety coefficient $\alpha$ can be calculated, e.g., from the newest value of hydrocarbon concentration and carbon monoxide concentration obtained by a discontinuous measuring means such as gas chromatograph and continuous measurement values of oxygen concentration obtained by an on-line oxygen analyzer. In this case, however, it is preferred that the larger safety coefficient $\alpha$ is to be kept taking into account the possible change in the minimum oxygen concentration with the composition change between the measurements.

In the method for controlling the explosion safety using the safety coefficient $\alpha$, when the safety coefficient $\alpha$ thus calculated becomes smaller than the predetermined safety margin, the safety coefficient $\alpha$ can be increased by a method which comprises changing the operation conditions of the reaction apparatus to lower the effluent oxygen concentration, a method which comprises changing the operation conditions of the hydrocarbon separator to lower the oxygen concentration, a method which comprises adding an inert gas such as nitrogen to the stream to be fed into the hydrocarbon separator to lower the oxygen concentration or the like. The reduction of the oxygen concentration at the outlet of the reaction apparatus can be accomplished by any method well known to those skilled in the art such as method involving the reduction of the flow rate of an oxygen-containing gas to be fed into the reaction apparatus, method involving the increase of the flow rate of hydrocarbon to be fed into the reaction apparatus and method involving the rise in the reaction temperature of the reaction apparatus.

On the contrary, if the safety coefficient α exceeds the predetermined margin, the safety coefficient α can be lowered to the desired range by operating the system counter to the foregoing procedures taking into account the economical efficiency of the process.

It is most preferred that the foregoing method involving the safety control over the exhaust stream from the hydrocarbon recovering step using the safety coefficient α be applied to the process for the production of maleic anhydride in combination with the foregoing reaction conditions (combination of concentration of hydrocarbon and oxygen to be fed into the reactor and the hydrocarbon conversion in the reactor or the effluent oxygen concentration). However, in the process for the production of maleic anhydride by a recycle process under reaction conditions different from those described above, too, if the reaction is effected under the conditions such that the productivity is as high as not less than 2.0 vol % as calculated in terms of concentration of maleic anhydride in the reaction product gas, the safety control over the exhaust stream from the hydrocarbon recovering step is preferably effected using the foregoing safety coefficient α.

It goes without saying that the foregoing safety coefficient α can be used in the explosion safety control not only over the exhaust stream from the hydrocarbon recovering apparatus but also over the mixture of carbon monoxide and hydrocarbon having the similar composition. For example, the effluent gas from the maleic anhydride recovering step in the present process, too, is a mixed gas containing carbon monoxide and hydrocarbon as main flammable gases. Thus, if the temperature, pressure and composition of such an effluent gas fall within the range to which the foregoing conditions can be applied, such an effluent gas can undergo similar safety control using the safety coefficient α.

In accordance with the process of the present invention, the productivity can be drastically enhanced while reducing the amount of hydrocarbon to be consumed in the production of maleic anhydride. Further, the amount of gases to be wasted, particularly carbon dioxide gas, can be drastically reduced. Moreover, the possibility of explosion of the exhaust gas after recovering hydrocarbon at the hydrocarbon recovering step can be eliminated, making it possible to provide a safe and efficient process for the production of maleic anhydride.

EXAMPLES

The present invention will be further described in the following examples, but the present invention should not be construed as being limited thereto.

Examples 1–3

Comparative Examples 1–4

A fluidized bed catalyst comprising a vanadium-phosphorus-based mixed oxide as an active component was prepared in accordance with the method described in JP-A-7-068179 (corresponding to U.S. Pat. No. 5,498,731). The catalyst thus obtained was then measured for the results of reaction with different compositions of the mixture of n-butane, oxygen and nitrogen in the following manner.

A quartz glass reaction tube was filled with 0.001 l of the catalyst. A mixed gas having a predetermined concentration was then allowed to flow through the reaction tube at a rate of 1.0 Nl/hr while the temperature of the reactor was being kept at a predetermined value by means of an electric furnace. After a predetermined period of time, the reactor effluent gas was sampled, and then analyzed by means of a gas chromatograph on-line connected to the reactor. The results are set forth in Table 1, which indicates the maleic anhydride concentration of the reactor effluent as a measure of productivity. As can be seen in Table 1, under the conditions of Examples 1, 2 and 3, the maleic anhydride selectivity can be kept high and the maleic anhydride concentration of the reactor effluent can be drastically enhanced as compared with the comparative examples. Comparative Example 1 exhibits a sufficiently high maleic anhydride concentration of the reactor effluent but exhibits very low maleic anhydride selectivity due to considerably high butane conversion. Comparative Example 2 exhibits a sufficiently high selectivity and maleic anhydride concentration but exhibits too high effluent oxygen concentration, giving an effluent gas falling within an explosive range. Thus, Comparative Example 2 is disadvantageous in respect to safety in operation.

TABLE 1

| Example No. | Butane concentration X (vol %) | oxygen concentration Y (vol %) | Reaction temperature (° C.) | Butane Conversion: Z (mol %) | MA selectivity: S (mol %) | Remaining oxygen concentration: W (vol%) | Y/X | MA concentration (vol %) |
|---|---|---|---|---|---|---|---|---|
| Example 1 | 7.9 | 30.0 | 414 | 66.4 | 66.6 | 10.9 | 3.8 | 2.8 |
|  |  |  | 431 | 68.7 | 62.5 | 7.0 |  | 3.2 |
|  |  |  | 448 | 79.2 | 58.1 | 3.0 |  | 3.3 |
|  |  |  | 454 | 81.8 | 56.2 | 2.0 |  | 3.3 |
| Example 2 | 12.0 | 39.4 | 418 | 54.1 | 64.4 | 11.9 | 3.3 | 3.9 |
|  |  |  | 436 | 66.7 | 60.6 | 6.3 |  | 4.4 |
|  |  |  | 454 | 76.5 | 56.3 | 0.0 |  | 4.6 |
| Example 3 | 20.6 | 24.2 | 365 | 13.0 | 67.7 | 13.0 | 1.2 | 1.8 |
|  |  |  | 382 | 18.0 | 66.1 | 8.6 |  | 2.3 |
|  |  |  | 400 | 23.5 | 63.6 | 3.7 |  | 2.9 |
| Comparative Example 1 | 7.9 | 40.0 | 451 | 89.2 | 56.6 | 8.8 | 5.1 | 3.6 |
|  |  |  | 464 | 94.8 | 51.5 | 6.3 |  | 3.5 |
|  |  |  | 481 | 98.7 | 42.4 | 3.9 |  | 2.9 |
| Comparative Example 2 | 8.0 | 58.5 | 430 | 84.0 | 62.2 | 28.9 | 7.3 | 3.8 |
|  |  |  | 446 | 96.1 | 50.5 | 23.3 |  | 3.4 |

TABLE 1-continued

| Example No. | Butane concentration X (vol %) | oxygen concentration Y (vol %) | Reaction temperature (° C.) | Butane Conversion: Z (mol %) | MA selectivity: S (mol %) | Remaining oxygen concentration: W (vol%) | Y/X | MA concentration (vol %) |
|---|---|---|---|---|---|---|---|---|
| Comparative Example 3 | 40.7 | 19.9 | 366 | 7.0 | 60.7 | 7.4 | 0.6 | 1.7 |
|  |  |  | 384 | 9.7 | 58.3 | 2.6 |  | 2.2 |
| Comparative Example 4 | 16.0 | 17.6 | 380 | 17.2 | 67.4 | 6.1 | 1.1 | 1.8 |
|  |  |  | 396 | 22.2 | 64.8 | 2.7 |  | 2.2 |

Butane conversion = (Number of n-butane consumed in the reaction)/(Number of n-butane supplied) × 100 (mol %)
MA selectivity = (Number of mols of maleic anhydride produced)/(Number of mols of n-butane consumed in the reaction) × 100 (mol %)
MA concentration = Concentration of maleic anhydride in the reactor effluent (vol %)

Example 4

A small-sized fluidized bed reactor having a length of 2.0 m and a diameter of 0.1 m longitudinally partitioned by 10 sheets of a metal mesh was filled with 0.85 kg of the same catalyst as used in Examples 1 to 3. A fluidized bed reaction was then effected with a mixture of oxygen and nitrogen being fed through the bottom of the reactor and butane being fed at a position 0.1 m above the bottom of the reactor. Each gas flow rate was controlled so that the total feed flow rate was 0.48 $Nm^3$/hr and the concentrations of butane, oxygen and nitrogen were 15 vol %, 25 vol % and 60 vol %, respectively.

Referring to the results obtained just after the start up of the reaction, the butane conversion and the maleic anhydride selectivity were 33 mol % and 63 mol %, respectively, at a reaction temperature of 405° C. The reaction continued at the same temperature. The results obtained after 2,000 hours were as stable as 31 mol % for butane conversion and 62 mol % for maleic anhydride selectivity.

Example 5

Mixtures of n-butane, carbon monoxide, oxygen and nitrogen having the composition set forth in Table 2 were prepared. The mixed gas thus prepared was then introduced into a preheated explosion vessel having a capacity of 1 l. In the explosion vessel, ignition was made with a 15 kV a.c. spark (0.01 sec., spark gap: 3 mm). With the rise in the pressure in the vessel, the mixed gas was checked to evaluate whether it exploded or not. The temperature of the explosion vessel was 80° C.

The results are set forth in Table 2.

TABLE 2

| Example No. | n-Butane (vol %) | Carbon monoxide (vol %) | Oxygen (vol %) | Nitrogen (vol %) | CO/BTA (vol /vol) | Total concentration of flammable gas (vol %) | Oxygen concentration in atmosphere (vol %) | Judgment on explosion |
|---|---|---|---|---|---|---|---|---|
| 1 | 0.41 | 7.70 | 9.65 | 82.25 | 95/5 | 8.1 | 10.5 | ◯ |
| 2 | 0.43 | 8.08 | 6.13 | 85.37 | 95/5 | 8.5 | 6.7 | ◯ |
| 3 | 0.47 | 8.84 | 5.90 | 84.80 | 95/5 | 9.3 | 6.5 | ◯ |
| 4 | 0.46 | 8.65 | 5.82 | 85.08 | 95/5 | 9.1 | 6.4 | X |
| 5 | 0.47 | 8.84 | 5.80 | 84.90 | 95/5 | 9.3 | 6.4 | X |
| 6 | 0.48 | 9.03 | 5.79 | 84.71 | 95/5 | 9.5 | 6.4 | X |
| 7 | 0.75 | 4.81 | 9.89 | 84.54 | 87/13 | 5.3 | 10.5 | ◯ |
| 8 | 0.78 | 4.98 | 7.52 | 86.72 | 87/13 | 6.0 | 8.0 | ◯ |
| 9 | 0.81 | 5.15 | 7.04 | 87.01 | 87/13 | 6.2 | 7.5 | ◯ |
| 10 | 0.83 | 5.31 | 6.93 | 86.93 | 87/13 | 6.4 | 7.4 | ◯ |
| 11 | 0.83 | 5.31 | 6.83 | 87.02 | 87/13 | 6.4 | 7.3 | X |
| 12 | 0.86 | 5.48 | 6.82 | 86.65 | 87/13 | 6.6 | 7.3 | X |
| 13 | 0.88 | 5.64 | 6.80 | 86.67 | 87/13 | 6.8 | 7.3 | X |
| 14 | 1.14 | 2.66 | 10.10 | 86.10 | 70/30 | 3.8 | 10.5 | ◯ |
| 15 | 1.20 | 2.80 | 8.06 | 87.94 | 70/30 | 4.0 | 8.4 | ◯ |
| 16 | 1.26 | 2.94 | 7.95 | 87.85 | 70/30 | 4.2 | 8.3 | ◯ |
| 17 | 1.26 | 2.94 | 7.86 | 87.94 | 70/30 | 4.2 | 8.2 | ◯ |
| 18 | 1.23 | 2.87 | 7.77 | 88.13 | 70/30 | 4.1 | 8.1 | X |
| 19 | 1.26 | 2.94 | 7.76 | 88.04 | 70/30 | 4.2 | 8.1 | X |
| 20 | 1.29 | 3.01 | 7.75 | 87.95 | 70/30 | 4.3 | 8.1 | X |

O/BTA (vol/vol) = Carbon monoxide concentration (vol %)/n-butane concentration (vol %)
Total concentration of flammable gas (vol %) = n-Butane concentration (vol %) + carbon monoxide concentration (vol %)
Oxygen concentration in the atmosphere (vol %) = (Oxygen concentration (vol %)/(Oxygen concentration (vol %) + nitrogen concentration (vol %)) × 100
Judgment on explosion: ◯: Exploded; X: Not exploded The maximum oxygen concentration in the atmosphere [oxygen concentration/(oxygen concentration+nitrogen concentration)×100 (vol %)] at which no explosion is observed when the total concentration of flammable gas [sum of n-butane concentration and carbon monoxide concentration (vol %)] varies from a value lower than the expected lower explosive limit to a value higher than the expected upper explosive limit corresponds to the minimum oxygen concentration of the mixed gas having the foregoing carbon monoxide/butane proportion.

Accordingly, the minimum oxygen concentration of mixed gases having various carbon monoxide/butane proportions can be determined from the results shown in Table 2. The results are set forth in Table 3.

TABLE 3

| CO/BTA (vol/vol) | minimum oxygen concentration (vol %) |
|---|---|
| 95/5 | 6.4 |
| 87/13 | 7.3 |
| 70/30 | 8.1 |

Example 6

Comparative Example 5

An embodiment of implication of the present invention was calculated as follows. In some detail, the material balance in the production of maleic anhydride at a rate of 1,000 kg per hour was determined.

In this embodiment of implication of the present invention, the concentrations of butane (X) and oxygen (Y) in all the gases to be fed into the reactor were 15 vol % and 25 vol %, respectively, the butane conversion (Z) was 35%, and the maleic anhydride selectivity was 63 mol %. The recovery of unreacted butane was accomplished by means of PSA (pressure swing adsorption apparatus) described in U.S. Pat. No. 4,987,239 at a percent recovery of 95% for butane, 84% for carbon dioxide and 20% for others. In this arrangement, butane, oxygen and air must be freshly fed at a flow rate of 397.3 $Nm^3/hr$, 1,102.1 $Nm^3/hr$ and 2,882.6 $Nm^3/hr$, respectively. The gas composition and flow rate at various positions were as set forth in Table 4. In this case, X+Y was 40 vol %, Y/X was 1.67, and the reactor effluent oxygen concentration (W) was 3.0 vol %.

As a comparative example, a conventional fluidized bed reaction involving no recovery of unreacted hydrocarbon was calculated. In some detail, calculation was made on the supposition that the concentration of butane and oxygen in all the gases to be fed into the reactor were 4.5 vol % and 20 vol %, respectively, the butane conversion was 83% and the maleic anhydride selectivity was 60 mol %. In this arrangement, butane, oxygen and air must be freshly fed at a flow rate of 458.7 $Nm^3/hr$, 0.0 $Nm^3/hr$ and 9,733.0 $Nm^3/hr$, respectively. The gas composition and flow rate at various positions were as set forth in Table 5.

As can be seen in Tables 4 and 5, in accordance with the foregoing embodiment of implication of the present invention, the amount of raw material butane, the amount of gas to be fed into the reactor, the amount of exhaust gas and the amount of carbon dioxide to be exhausted for the production of the same amount of maleic anhydride can be drastically reduced, i.e., to about 87%, about 69%, about 29% and about 73%, respectively, as compared with the conventional case. On the other hand, the ratio of the oxygen amount from the pure oxygen to the total oxygen amount in the reactor feed among oxygen sources was kept at about 65%. This demonstrates that the economical efficiency of the entire process is extremely enhanced.

TABLE 4

| Component | Reactor inlet (fresh Feed) | | Reactor inlet (total feed) | | Reactor effluent | |
|---|---|---|---|---|---|---|
| | $Nm^3/hr$ | Vol % | $Nm^3/hr$ | Vol % | $Nm^3/hr$ | Vol % |
| Butane | 397.3 | 9.1 | 1,051.5 | 15.0 | 688.7 | 9.2 |
| Oxygen | 1,707.2 | 39.0 | 1,752.5 | 25.0 | 226.3 | 3.0 |
| Nitrogen | 2,249.9 | 51.3 | 2,812.4 | 40.1 | 2,812.4 | 37.6 |
| Argon | 26.8 | 0.6 | 33.5 | 0.5 | 33.5 | 0.4 |
| Maleic anhydride | | | | | 228.6 | 3.1 |
| Carbon monoxide | | | 73.2 | 1.0 | 366.1 | 4.9 |
| Carbon Dioxide | 0.9 | 0.0 | 1,286.8 | 18.4 | 1,530.9 | 20.5 |
| Water | | | | | 1,585.5 | 21.2 |
| Total | 4,382.1 | 100.0 | 7,009.9 | 100.0 | 7,472.0 | 100.0 |

TABLE 5

| Component | Reactor inlet (fresh feed) | | Reactor inlet (total feed) | | Reactor effluent | |
|---|---|---|---|---|---|---|
| | $Nm^3/hr$ | Vol % | $Nm^3/hr$ | Vol % | $Nm^3/hr$ | Vol % |
| Butane | 458.7 | 4.5 | 458.7 | 4.5 | 78.0 | 0.7 |
| Oxygen | 2,043.4 | 20.0 | 2,043.4 | 20.0 | 420.0 | 3.9 |
| Nitrogen | 7,596.1 | 74.5 | 7,596.1 | 74.5 | 7,596.1 | 71.0 |
| Argon | 90.5 | 0.9 | 90.5 | 0.9 | 90.5 | 0.8 |
| Maleic anhydride | | | | | 228.4 | 2.1 |
| Carbon monoxide | | | | | 332.3 | 3.1 |
| Carbon dioxide | 2.9 | 0.0 | 2.9 | 0.0 | 279.8 | 2.6 |
| Water | | | | | 1,675.2 | 15.7 |
| Total | 10,191.7 | 100.0 | 10,191.7 | 100.0 | 10,700.7 | 100.0 |

The safety coefficient α calculated from the composition of the exhaust gas after recovering hydrocarbon at the hydrocarbon recovering step in Table 4 is 0.32. This demonstrates that this composition has lower oxygen concentration in the atmosphere than the minimum oxygen concentration and thus falls outside of explosive range. The lower explosive limit of this gas is calculated by Le Chateliers law to be about 6.6 vol %. This gas has a total flammable gas concentration of 10.8 vol %, which is higher than the lower explosive limit. Accordingly, it is made obvious that the process of the present invention which comprises keeping the oxygen concentration in the atmosphere lower than the minimum oxygen concentration must by employed to control the explosion safety of this composition.

What is claimed is:

1. A process for the production of maleic anhydride, which comprises:

reacting a hydrocarbon in gaseous state with an oxygen-containing gas in the presence of a catalyst in a reactor to produce an effluent reaction gas containing maleic anhydride;

recovering maleic anhydride from the reaction gas;

recovering at least 90% of the unreacted hydrocarbon from the gas remaining after recovery of the maleic anhydride with the production of an exhaust gas; and returning the hydrocarbon thus recovered to the reactor for re-use;

wherein said reaction is effected under the conditions such that the hydrocarbon concentration X (vol %) and oxygen concentration Y (vol %) in all the gases to be fed into the reactor, the hydrocarbon conversion Z (%) in the reactor and the oxygen concentration W (vol %) in all the effluent gases from the reactor satisfy the following relationships:

$Y > 20$,
$X + Y \leq 70$,
$1 \leq Y/X \leq 5$, and
$20(Y-10)/X \leq Z \leq 25Y/X$ or $2 \leq W \leq 10$.

2. The process according to claim 1, wherein a nitrogen concentration in all the gases to be fed into the reactor is at least 30 vol %.

3. The process according to claim 1, wherein said hydrocarbon is a saturated hydrocarbon having four carbon atoms.

4. The process according to claim 1, wherein said catalyst is a vanadium-phosphorus-based mixed oxide catalyst.

5. The process according to claim 1, wherein said reactor for reacting hydrocarbon with oxygen-containing gas is a fluidized bed reactor.

6. The process according to claim 1, which comprises recovering hydrocarbon from said remaining gas using a hydrocarbon recovering apparatus, and then returning it to the reactor.

7. The process according to claim 6, wherein said hydrocarbon recovering apparatus is a membrane separator, pressure swing adsorption apparatus, vacuum swing adsorption apparatus or temperature swing adsorption apparatus.

8. The process according to claim 1, wherein more than one-half of the gas remaining after recovery of maleic anhydride, other than hydrocarbon, is not recovered and returned to the reactor.

9. The process according to claim 1, wherein the oxygen concentration Y is 25 vol. % or more.

* * * * *